(12) United States Patent  
Fitter et al.

(10) Patent No.: US 6,220,141 B1  
(45) Date of Patent: Apr. 24, 2001

(54) LIQUID PROJECTILE LAUNCHER

(75) Inventors: Johan Christiaan Fitter; Patricia Ann Crossley, both of Sandton (ZA)

(73) Assignee: Injectiles Limited (GB)

( * ) Notice: Subject to any disclaimer, the term of this patent is extended or adjusted under 35 U.S.C. 154(b) by 0 days.

(21) Appl. No.: 09/043,843

(22) PCT Filed: Sep. 30, 1996

(86) PCT No.: PCT/GB96/02406

§ 371 Date: Jul. 10, 1996

§ 102(e) Date: Jul. 10, 1998

(87) PCT Pub. No.: WO97/12194

PCT Pub. Date: Apr. 3, 1997

(30) Foreign Application Priority Data

Sep. 28, 1995 (ZA) .................................... 95/8165

(51) Int. Cl.[7] .......................................... F41F 1/00
(52) U.S. Cl. ................................................. 89/8
(58) Field of Search ...................................... 89/8

(56) References Cited

U.S. PATENT DOCUMENTS 5,331,879 * 7/1994 Loffler ............................. 89/8

FOREIGN PATENT DOCUMENTS

0242501 * 10/1987 (EP) .

* cited by examiner

*Primary Examiner*—Jack W. Lavinder  
(74) *Attorney, Agent, or Firm*—Blakely, Sokoloff, Taylor & Zafman

(57) ABSTRACT

A fluid projectile launcher (10) comprises a barrel having an open end and a closed end defining a breech portion (50). The breech portion (50) is arranged to hold a dosage of fluid (56) in the form of an ionizing medium for rendering the fluid electrically conductive and an active substance which induces a physiological reaction in living organisms. The projectile launcher (10) includes a launching initiation circuit in the form of a capacitor (22) and an inductance (36), and a pair of electrodes (38A, 38B) forming part of the breech portion (50). Trigger means (40) are provided for allowing the energy storage means (22) to discharge into the dosage of fluid (56) in the breech portion (50) via the electrodes (52, 38A, 38B) so as to cause the dosage of fluid (56) to be projected from the open end of the barrel as a fluid projectile. The leads (38A, 38B) connecting the capacitor (22) and inductance (36) are arranged in a radially symmetrical pattern about a tubular first electrode so as to create an electromagnetic field which is functionally symmetrical in the plane normal to the central axis of the barrel. The launcher may be in the form of a portable hand held device.

17 Claims, 1 Drawing Sheet

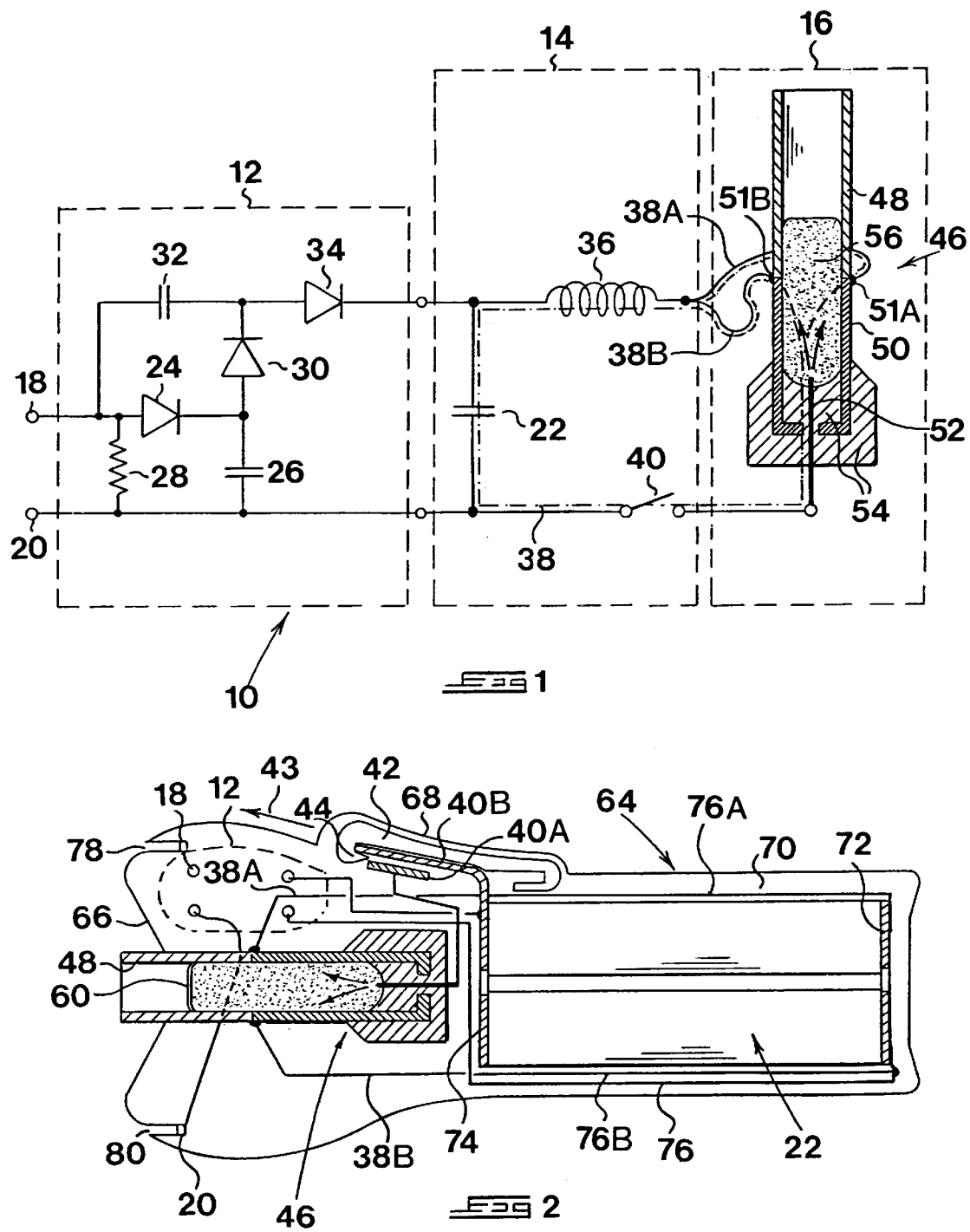

LIQUID PROJECTILE LAUNCHER

BACKGROUND TO THE INVENTION

A number of applications clearly show that water droplets projected at high velocity can retain their integrity until impacting on a desired target a selected distance away. For example, cutting machines using high pressure air and/or water jets have been successfully used for many years. Vaccination guns based on hydraulic propulsion have also become commonplace. Due to the number of conversions prior to application, energy is, however, not always utilised efficiently.

Direct energy conversion from electrical to kinetic has been applied in the case of metallic projectile launchers utilising a successively pulsed array of solenoid coils to provide the requisite accelerating force. It has also been applied in conjunction with a water propellant to effect the discharge of a small gun—the water first having been made conductive by the addition of salt—and by passing through an electrical current to bring about an electric arc, thereby promoting the requisite surge of electric current required to eject a solid projectile from the barrel at high velocity.

A water-arc launcher utilising this principle is described in a magazine article by Peter Graneau. Electronics and Wireless World, June 1989, pp 556–559. However, the side-mounted current connector in this version results in pronounced asymmetry in the axial current flow upon launching, causing the liquid charge to scatter widely upon emerging from the barrel, and thereby rendering the device ineffective for use as a globular liquid projectile launcher. The use of a solid projectile in conjunction with the water charge incorporated in the water gun featured in this article is also somewhat impractical. While the water charge amounts to a rather modest 3.8 g, the energy requirement to propel the total charge at 1000 meters per second would necessitate capacitor charge to a voltage sufficient to sustain an electric arc, amounting to a half to a full farad of capacitance, and capable of discharging in sizable fractions of 100 kA. This would weigh many kilograms, and make equipment based on this type of approach too heavy for use in applications requiring a high degree of portability.

SUMMARY OF THE INVENTION

According to a first aspect of the invention there is provided a fluid projectile launcher comprising a barrel having an open end and a closed end defining a breech portion arranged to hold a dosage of fluid, and a launching initiation circuit including energy storage means, energy application means forming part of the breech portion, symmetrical thrust-generating and perpetuating means, and trigger means for allowing the energy storage means to discharge into the dosage of fluid in the breech portion via the energy application means so as to cause the dosage of fluid to be symmetrically thrusted from the open end of the barrel as a fluid projectile.

Preferably, the energy application means includes first and second electrodes which are insulated from one another bar their individual electrical connection via the dosage of fluid, and which are symmetrical about a central axis of the barrel, the energy storage means includes a capacitor, and the symmetrical thrust generating and perpetuating means includes an array of electrical leads connected symmetrically to the first and second electrodes relative to the central axis of the barrel so as to create an electromagnetic field which is functionally symmetrical in a plane normal to the central axis of the barrel.

Conveniently, the breech portion is dimensioned and the energy application means is positioned to accommodate a fluid dosage having a maximum mass of 1 gram.

Advantageously, the breech portion includes a tubular electrically conductive portion defining the first electrode, the second electrode comprises an electrically conductive pin substantially coincident with the central axis of the barrel and extending into a base of the breech portion, and the array of electrical leads including at least a first pair of leads connected equi-angularly in a radially symmetrical pattern around the tubular first electrode and a second lead connected to the second electrode.

The invention extends to a fluid projectile launcher comprising a barrel having an open end and a closed end defining a breech portion arranged to hold a dosage of fluid, and a launching initiation circuit including energy storage means, energy application means forming part of the breech portion, and trigger means for allowing the energy storage means to discharge into the dosage of fluid in the breech portion via the energy application means so as to cause the dosage of fluid to be launched from the open end of the barrel as a fluid projectile, the breech portion being dimensioned and the energy application means being positioned to accommodate a fluid dosage having a maximum mass of 1 gram, preferably having a maximum mass of 0.5 grams, and more preferably having a maximum mass of 0.1 grams.

Typically, the energy storage means includes a capacitor and an inductance for controlling the rate of discharge of arc current across the first and second electrodes, the arc current having a waveform including at least one half sinusoid.

The waveform of the discharge arc current may include a plurality of half sinusoids defining at least one damped oscillation.

Preferably, the launching initiation circuit includes a pair of input terminals arranged to be connected to a power supply, and conditioning means for conditioning the power from the power supply, the conditioning means including a voltage multiplying rectifier.

The fluid projectile launcher may be in the form of a portable hand-held device including a handle, and the trigger means includes a sliding switch having a pair of fusible contacts, and a separator for prying open the contacts after use.

The barrel may have a diameter from 2 mm to 3.5 mm.

According to a still further aspect of the invention there is provided a primed fluid projectile launcher comprising a barrel having an open end and a closed end defining a breech portion holding a dosage of fluid, and a launching initiation circuit including energy storage means, energy application means forming part of the breech portion, and trigger means for allowing the energy storage means to discharge into the dosage of fluid in the breech portion via the energy application means so as to cause the dosage of fluid to be launched from the open end of the barrel as a fluid projectile, the dosage of fluid comprising an ionising medium for rendering the fluid electrically conductive and an active substance which induces a physiological reaction in living organisms.

The active substance may include at least one of the following, namely a drug, a plant or animal protection agent such as a vaccine or insecticide, a nutrient, a poison, a pain-inducing substance, or a disabling agent.

The invention extends to a method of inducing a physiological reaction in a living organism including the steps of providing a fluid projectile launcher comprising a barrel having an open end and a closed end defining a breech portion, and a launching initiation circuit including energy storage means, energy application means forming part of the breech portion, and trigger means, loading the breech portion of the fluid projectile launcher with a dosage of fluid, the fluid including an ionising medium for rendering the fluid electrically conductive and an active substance which induces a physiological reaction in the living organism, aiming the liquid projectile launcher at a target defined by the living organism, and activating the trigger means so as to allow the energy storage means to discharge into the dosage of fluid in the breech portion via the energy application means so as to cause the dosage of fluid to be thrusted from the open end of the barrel as a fluid projectile.

The method may include the initial step of charging the energy storage means from an external power supply.

BRIEF DESCRIPTION OF THE DRAWINGS

Embodiments of the invention are described below, by way of example only, and with reference to the accompanying drawings in which:

FIG. 1 is a schematic and circuit diagram of a liquid projectile launcher of the invention; and FIG. 2 is a cross-sectional side view of one embodiment of a typical liquid projectile launcher of the invention.

DESCRIPTION OF EMBODIMENTS

Referring first to FIG. 1, a liquid projectile launcher 10 has three main components, namely a voltage tripling rectifier indicated in broken outline at 12, an energy storage device indicated in broken outline at 14 and a barrel and breech assembly indicated in broken outline at 16.

An AC utility supply typically having a potential of 240 volts at a frequency of 50 hertz is briefly connected across input terminals 18 and 20 of the voltage tripling rectifier 12. The voltage tripling rectifier allows the capacitor 22 to charge to approximately 1 kV. In an alternative version of the invention, a battery supply is used as a power source to charge the capacitor 22, in which case an inverter needs to be included to provide the necessary AC supply across the terminals 18 and 20.

The voltage tripling rectifier works in the following manner. If the potential at terminal 18 is positive and rising in respect of terminal 20, diode 24 conducts so as to charge a capacitor 26, with a small current flowing via a bridging resistor 28. As soon as the polarity at the terminals 18 and 20 is reversed, this causes a diode 30 to conduct thereby charging a capacitor 32. On the following reversal, both diode 34 and diode 30 conduct, and the main energy storage capacitor 22 will be partly charged. Thereafter, successive reversals of the AC supply will pass a certain amount of charge via the capacitor "bucket brigade", until the energy storage capacitor 22 is fully charged after a few seconds.

The capacitors 26 and 32 have typical values of 1 to 5 microfarads, whilst the main charge storage capacitor 22 has a value of between 100 and 250 microfarads, depending on the charge required to launch the liquid projectile. The diodes 24, 30 and 34 are typically inexpensive low current devices rated at about 1.2 kV PIV. It is essential that the diode 34 has a very low reverse leakage at full applied peak reverse voltage so as to prevent discharge of the main charge storage capacitor 22 after charging is complete and the device is disconnected from the power source. The resistor 28 ensures that there will be zero potential across the terminals 18 and 20 once they are unplugged from the power source by providing a discharge path for the capacitors 26 and 32.

The main energy storage capacitor preferably comprises a metallised plastic film capacitor, and may alternatively be in the form of a high current electrolytic capacitor or ceramic capacitor. The main criteria of the capacitor 22 being that is should have a high discharge delivering capability, low leakage, modest self-inductance and the smallest possible physical dimensions.

The inductance 36 may be entirely incorporated into the self-inductance of the capacitor 22, together with the interconnecting lead inductance of the entire energy storage circuit indicated in chain outline at 38, and including electrode leads 38A and 38B defining split, but equal current paths which form an effective closed loop on closure of trigger switch 40. Alternatively, the inductance may include a specific inductor incorporated conveniently in series with the other inductances. As is more clearly illustrated in FIG. 2, the switch 40 comprises a pair of broad contacts in the form of a fixed contact 40A and a hinged contact 40B which are brought into contact with one another by bringing suitable pressure to bear against a sliding mechanism 42 in the direction of arrow 43. Under-engineering of the switch contacts 40A and 40B is not necessarily a disadvantage, in that on closure, the current across the switch contacts will cause partial welding of the mating faces, thereby preventing contact bounce and also ensuring low contact resistance. A wedge-shaped separator 44 extends rearwardly from a front end of the slider 42 so as to pry open the contacts 40A and 40B after use. An additional contact cleaning mechanism may be used in applications where frequent use of the liquid projectile launcher is required.

The barrel and breech assembly 16 is in the form of a tube having a front electrically insulating portion 48 and a rear electrically conductive breech portion 50 serving as a first electrode. The leads 38A and 38B terminate in diametrically opposed connection points 51A and 51B on the outer perimeter of the breech portion 50, adjacent the insulating portion 48. The symmetry of the electrical connection relative to the axis of the tube allows for an axial propulsion current which is substantially symmetrical about the inner circumference of the first electrode 50.

Located at the base of the breech portion 50 is an electrically conductive pin 52 which acts as a second electrode positioned centrally along the axis of the tube so as to co-operate advantageously with the first electrode to produce a symmetrical current and consequent symmetrical thrust behind the liquid projectile upon launching. This second electrode is surrounded by a spacing insulator and mechanical buffer 54 formed from highly resilient impact resisting material. It may be desirable to connect the inductor 36 close to the open end of assembly 16, in which case the electrically insulating portion 40 may be shortened or even omitted while at the same time the conductive breech portion 50 may be extended in its place.

The first, and smaller portion of the energy applied to the electrodes 50 and 52 raises the temperature of a tiny fraction of water between the electrodes to that required to form plasma, being in the order of 3000 to 6000° C., with the balance and larger portion delivering the requisite thrust to accelerate the water and to drive it out of the launch assembly 16 at high speed. The process of heating, forming plasma and ejection follows in a naturally, self-regulating sequence upon application of the high voltage potential. Symmetrical current distribution ensures practically all the water is ejected in globular form, remaining intact until impacting the selected target at high velocity.

The rate of rise of pressure against the inner breech and tube assembly 46 is exceptionally high, with the result that particularly resilient material, such as high impact resisting nylon or polycarbonate plastic is required.

Upon discharge of the capacitor 22, the arc current easily exceeds 25000 amperes, resulting in immense acceleration being applied to the liquid slug 56, which can propel the liquid from the barrel at a velocity exceeding 1000 m/s. The actual velocity depends on the size of the body or slug of liquid 56, the quality of finish of the inside bore of the barrel, the symmetry of current flow in the barrel and the amount of energy stored in the capacitor 22.

The performance of a well-crafted liquid projectile launcher can be predicted with a reasonable degree of accuracy.

Assuming a single drop of water is to be accelerated to 1000 meters per second, the energy required will be:

$$E = \tfrac{1}{2} mv^2 \text{ where } \quad E = \text{energy in joules}$$
$$m = \text{mass in kg}$$
$$v = \text{velocity in m/s}$$

Assuming there are 20 drops of water in a milliliter, thus:

$$E = \frac{1}{2} \times \frac{0.05}{1000} \times 1000^2 = 25 \text{ joules}$$

Assuming a mechanical efficiency of 50%, and an electrical efficiency of 75%, the energy stored in the capacitor must be $$25 \times \frac{100}{50} \times \frac{100}{75} = 67 \text{ joules}$$

The energy stored in a capacitor is:

$$E = \tfrac{1}{2} CV^2 \text{ where } \quad E = \text{energy in joules}$$
$$C = \text{capacitance in farads}$$
$$V = \text{potential in volts}$$

Assuming the capacitor is charged to 1000 volts, then:

$$C = 2 \frac{E}{V^2} = \frac{2 \times 67 \times 10^6}{1000^2} = 134 \ \mu F$$

A capacitor with the nearest standard value, being 150 $\mu$F, would probably be used.

The advantage of employing high voltage is reduced capacitance. For example, at 2000 volts the capacitance would be:

$$\frac{2 \times 67 \times 10^6}{2000^2} = 33.5 \ \mu F$$

A doubling in voltage resulting in a quartering of the capacitance value required implies that the use of some tens of thousands of volts may be advantageous. A 150 $\mu$F, 1000V dc capacitor is not too large for incorporation into a hand-held appliance, however.

Inductor 36 is included to provide a means for controlling the arc current, and thereby tailoring the rate of accelerating to particular circumstances. The inductor could possess a value in the order of a few tenths up to several $\mu$H. It may be desirable to vary the acceleration in order to obtain a desired effect on the spread of the liquid projectile in flight, in which case the value of inductance could be increased or decreased, as appropriate.

Assuming a capacitance of 150 micro farads, and an inductance of 0.5 micro-henries, then the resonant frequency would be:

$$F_{res} = \frac{1}{2\pi\sqrt{LC}} = 18.4 \text{ Khz}$$

The polarity of the arc current would then reverse every 27.2 micro-seconds, in a damped oscillation.

At low inductance, the elasticity of the launch tube assembly would be severely tested, and it may prove advantageous to increase the inductance significantly, and at the same time lengthen the conducting portion of the barrel to allow for the increased time required for the liquid projectile to achieve the desired velocity.

It may be desirable to launch the liquid projectile within the time of the first half sinusoid, in which case the length of the conductive breech portion 50 would have to be tailored to provide a conductive path while the projectile accelerates from stand-still to 1000 meters per second, in, for example, 27.2 microseconds. This would involve some trial and error work since the rate of acceleration is influenced by diameter-to-length ratio of the barrel assembly, as well as the pin 42 and buffer 54 dimensional aspects, material resilience and arc current.

Conversely, the projectile may be accelerated over, say, five half sinusoids, in which case the projectile would take 136 micro-seconds to reach maximum speed, which is likely to be considerably less than 1000 meters per second, and the launch tube would typically be much longer and narrower. The projectile would be subjected to a series of impulses of rapidly diminishing strength, thereby varying the shape of the emerging liquid projectile.

It is important to bear in mind that electric arcs do possess comparatively stable voltage characteristics, having an impedance which tends to vary inversely with current. The arc voltage lies in the region of 60 volts, and would rise only marginally with increase in current and with increase in arc length.

As the energy stored in the capacitor 22 oscillates via the inductor 36 and the arc load, it is dissipated in the arc and the associated circuitry resistance. This LC circuit forms an approximate constant power source providing an efficient means of transforming a high voltage source with a falling characteristic to a comparatively steady 60 volts across the arc.

Referring now to FIG. 2, a typical liquid projectile gun 64 is shown. The gun 64 resembles a conventional hand-held flashlight having a non-threatening appearance, which may enhance its effectiveness as a personal self-defence weapon.

The barrel and breech assembly 46 occupies the same position as would normally be occupied by a flashlight bulb, and the illusion is enhanced by the inclusion of a reflector 66. The sliding switch 42 is housed beneath the plastics or rubber covering 68, which forms part of a rubberised housing 70 closely resembling a conventional flashlight housing.

The capacitor 22 is housed in the handle portion of the gun, which is normally where the batteries of a similar flashlight are housed. Electrical connections to the capacitor 22 are made via conductive end plates 72 and 74, with parallel leads 76A and 76B, (corresponding to current paths 38A and 38B respectively), having substantially matching resistive as well as inductive characteristics, extending from the end plate 72 to the inductor 36 and the hinged terminal 40B extending directly from the end plate 74.

In the present embodiment the leads 76A and 76B are diametrically opposed with respect to the central axis of the breech and tube assembly 46. A favourable reduction in circuit resistance, as well as inductance, together with an improvement in the current flow symmetry is achieved by increasing the number of paralleled conductors, for example, to three conductors radially equi-spaced at 120° from one another, to four spaced at 90° from one another, and by logical extension arriving at a substantially enclosing coaxial arrangement for best possible results.

The voltage tripling rectifier circuit 12 is housed behind the reflector 66 opposite the inductor 36. The input terminals 18 and 20 are located within recesses 78 and 80 located at the outer periphery of the reflector 66, and are arranged to mate with a special power source adaptor (not shown) so as to provide contact between the terminals 18 and 20 and the utility power source so as to charge the capacitor 22.

In use, the gun is held in the manner of a flashlight, and is aimed at the desired target. The sliding mechanism 42 is operated by pressing the thumb forward against the rubber cover 68 in the direction of the arrow 43. As was described previously, return of the sliding mechanism 42 separates the contacts of the switch 40.

Replenishment of liquid 56 is carried out by means of a suitable dispenser, which is calibrated so as to deposit a correctly measured dose of liquid into the barrel and breech assembly 46. It is clear from the above description that the gun requires manual recharging before each successive discharge. It is possible to achieve a degree of repetition by constructing an appropriate feeding system incorporating a liquid reservoir or magazine so as to automatically replenish the liquid as well as recharging the capacitor 22 after each successful operation. Alternatively, a multiple barrel-capacitor system may be devised. As the liquid projectile launcher of the invention is electrically detonated, this makes it particularly well suited to remote detonation.

Several different barrel constructions are possible. In one alternative construction, the non-conductive barrel portion 48 may be replaced with a conductive portion which extends from the conductive breech portion 50. As a further option, additional barrel sections may be provided for providing additional guidance and velocity to the liquid projectile. These barrel sections may include electrically conductive and insulating sections which are fitted alternately to one another, whereby the conductive sections provide an additional accelerating force for the liquid projectile, being optionally connected to additional energy storage circuits.

In a particular embodiment, the conductive breech portion may be constructed of solid metal. Alternatively, it may be constructed of a non-conductive material, for example, plastic, having a metal lining inside the bore, extending outwards where required for the electrical connection.

In another embodiment described, the inner barrel diameter may be between 2 to 3.5 mm and the overall barrel length may be from 20 to 50 mm so as to accommodate a single drop (0.05 ml) of water. Naturally, depending on the rating of the energy source, these dimensions may be scaled up or down.

In a further embodiment the bobbin of the capacitor 22 may be enlarged sufficiently to allow the entire tubular barrel assembly 46 to be housed inside the inner bore of the capacitor bobbin thereby reducing the effective length of the interconnections and maximising efficiency.

It seems unlikely that, on its own, a single drop of water will have a significant effect on a human or animal target. Certainly, a drop of water travelling at 1000 m/s, which is about three times the speed of sound, will pass through all but the heaviest clothing and will easily pass through hair or fur. The addition of reasonable strong acid. (pH less than about 3), or reasonably strong base, (pH greater than about 11), can alter the effect dramatically, by providing a pain stimulus of great intensity upon being driven into the skin. Such acids would include all the strong mineral acids as well as organic acids such as formic acid. Even the acid constituents of a mild acid such as orange juice could suffice. Bases such as ordinary washing soda, ammonia, and the like would be equally effective. Common solvents such as acetone could also provide a pain stimulus. By way of illustration, the effect of application of any of these substances to, say, a small cut in the finger, is well known.

The addition of organic irritation-specific substances or pharmaceutical drugs possessing pain inducing properties may prove advantageous. These may include capsaicin, a compound obtained from chili peppers—capsicum minimum—which causes a fierce burning sensation. Substances found in the stings of bees, wasps and hornets, and indeed the common nettle, which include histamine, serotonin and acetylcholine, acting in concert, can induce instant severe pain, despite the almost infinitesimal amounts of active component involved. Histamine is highly effective since it mimics the body's very own pain inducing stimulation process.

Histamine is conventionally dispensed in the form of histamine disphosphate, $C_5H_9N_3.2H_3PO_3$, or as the dihydrochloride salt, although it is light-, as well as temperature-sensitive.

The effect on an attacker from a discharge, at short to medium range, is likely to be immediate and profound. Firing results in a bright flash of light, a loud audio report followed immediately by the onset of intense localised pain. The combination provides a convincing simulation of firearm discharge. In the case of some irritation-specific substances, a localised entry wound may take the form of a burn or a weal. In addition, there may be a generalised reaction to these substances resulting in shock with associated mental impairment. Significantly, these conditions are generally reversible.

It may be advantageous to use the present liquid projectile launcher in the application or administration of anaesthetics, tranquilizers, and the like, as well as other drugs of a preventative nature—even dyes and colorants—to human as well as animal recipients.

Unwanted interaction between electrically induced activity and the substances included in the liquid projectile may be minimised by inclusion of specific barrier arrangements applied and/or located to maintain desired separation.

In the case of dyes, colourants, as well as other substances used for surface treatment of objects, an effectively continuous feed of the projected substance may be employed, including a means of providing corresponding electrical energy required by the process. The liquid for dispensing is fed into the mechanism in sequential doses, each dose being individually launched by carefully timed electrical discharges, at high speed, to provide an effect of continuity of feed.

What is claimed is:

1. A fluid projectile launcher, comprising a barrel having an open end and a closed end defining a breech portion arranged to hold a dosager of fluid, and a launching initiation circuit including energy storage means, energy application means forming part of the breech portion, symmetrical thrust-generating and perpetuating means, trigger means for allowing the energy storage means to discharge into the dosage of fluid in the breech portion via the energy application means in the form of an arc current so as to cause the dosage of fluid to be symmetrically thrusted from the open end of the barrel by the symmetrical thrust-generating and perpetuating means as a fluid projectile, and discharge control means for controlling the rate of discharge of arc current across the energy application means, the breech portion being dimensioned and the energy application means being positioned to accommodate a discrete fluid dosage having a predetermined mass.

2. A fluid projectile launcher according to claim 1 in which the energy application means includes first and second electrodes which are insulated from one another bar their individual electrical connection via the dosage of fluid, and which are coaxial with a central axis of the barrel, the energy storage means includes a capacitor, the discharge control means includes an inductance and the symmetrical thrust-generating and perpetuating means includes an array of electrical leads connected symmetrically to the first electrode with respect to a plane which is normal to the central axis of the barrel so as to create an electromagnetic field which is functionally symmetrical in such a plane.

3. A fluid projectile launcher according to claim 2 in which the breech portion includes a tubular electrically conductive portion defining the first electrode, the second electrode comprises an electrically conductive pin substantially coaxial with the central axis of the barrel and extending into a base of the breech portion, and the array of electrical leads includes at least a first pair of leads connected equi-angularly in a radially and axially symmetrical configuration around the tubular first electrode, and a second lead connected to the second electrode.

4. A fluid projectile launcher according to claim 1 in which the energy storage means includes a storage capacitor, the discharge control means comprises an inductance and the arc current has a discharge waveform including at least one half sinusoid.

5. A fluid projectile launcher according to claim 4 in which the discharge waveform of the arc current includes a plurality of half sinusoids defining at least one damped oscillation for subjecting the liquid projectile to a series of impulses of diminishing strength.

6. A fluid projectile launcher according to claim 1 in which the launching initiation circuit includes a pair of input terminals arranged to be connected to a power supply, and conditioning means for conditioning the power from the power supply, the conditioning means including a voltage multiplying rectifier.

7. A fluid projectile launcher according to claim 6 in which the power supply is an external AC mains supply.

8. A fluid projectile launcher according to claim 6 in which the power supply is an inverted battery supply.

9. A fluid projectile launcher according to claim 6 in which the voltage multiplying rectifier comprises first and second charging capacitors which are alternately charged via respective first and second diodes so as to successively build up charge in the storage capacitor.

10. A fluid projectile launcher according to claim 1 which is in the form of a portable hand-held device including a handle, and the trigger means includes a sliding switch having a pair of fusible contacts, and a separator for prying open the contacts after use.

11. A fluid projectile launcher according to claim 1 in which the barrel has an internal diameter from 2 mm to 3.5 mm.

12. A fluid projectile launcher according to claim 1 in which the barrel has an effective length of 20 mm to 50 mm.

13. A primed fluid projectile launcher comprising a barrel having an open end and a closed end defining a breech portion holding a dosage of fluid, and a launching initiation circuit including energy storage means, energy application means forming part of the breech portion, and trigger means for allowing the energy storage means to discharge into the dosage of fluid in the breech portion via the energy application means in the form of an arc current so as to cause the dosage of fluid to be launched from the open end of the barrel as a fluid projectile, and discharge control means for controlling the rate of discharge of arc current across the energy application means, the breech portion being dimensioned and the energy application means being positioned to accommodate a discrete fluid dosage having a predetermined mass, and the dosage of fluid comprising an ionising medium for rendering the fluid electrically conductive and an active substance which induces a physiological reaction in living organisms.

14. A primed fluid projectile launcher according to claim 13 in which the substance includes one of the following, namely a drug, a plant or animal protection agent such as a vaccine or insecticide, a nutrient, a poison, a pain-inducing substance, or a disabling agent.

15. A method of inducing a physiological reaction in a living organism including providing a fluid projectile launcher comprising a barrel having an open end and a closed end defining a breech portion, and a launching initiation circuit including energy storage means, energy application means forming part of the breech portion, trigger means, and discharge control means for controlling the rate of discharge of arc current across the energy application means, loading the breech portion of the fluid projectile launcher with a discrete dosage of fluid having a predetermined mass, the fluid including an ionising medium for rendering the fluid electrically conductive and an active substance which induces a physiological reaction in the living organism, aiming the liquid projectile launcher at a target defined by the living organism, and activating the trigger means so as to allow the energy storage means to discharge in a controlled fashion into the dosage of fluid in the breech portion via the energy application means in the form of an arc current so as to cause the dosage of fluid to be thrusted from the open end of the barrel as a fluid projectile.

16. A method according to claim 15 in which the active substance includes at least one of the following, namely a drug, a plant or animal protection agent such as a vaccine or insecticide, a nutrient, a poison, a pain-inducing substance, or a disabling agent.

17. A method according to claim 15 which includes charging the energy storage means from an external power supply.

* * * * *